United States Patent [19]
Lee et al.

[11] Patent Number: 5,723,645
[45] Date of Patent: Mar. 3, 1998

[54] METHOD FOR PREPARING 3-AMINOPROPANE PHOSPHORIC ACID

[75] Inventors: Ok Sub Lee, Anyang; Young Hun Byon; Bo Sub Lee, both of Yongin; Jong Eon Hong; Jae Suk Ko, both of Seoul; Yun Ki Cho, Yongin; Ho Lee, Suwon, all of Rep. of Korea

[73] Assignee: Pacific Corporation, Seoul, Rep. of Korea

[21] Appl. No.: 744,352

[22] Filed: Nov. 4, 1996

[30] Foreign Application Priority Data

Sep. 5, 1996 [KR] Rep. of Korea ............. 1996-38496
Oct. 26, 1996 [KR] Rep. of Korea ............. 1996-48938

[51] Int. Cl.$^6$ ............................................. C07F 9/09
[52] U.S. Cl. ..................... 558/132; 558/133; 558/166
[58] Field of Search .............................. 558/132, 166

[56] References Cited

FOREIGN PATENT DOCUMENTS

| | | |
|---|---|---|
| 60-199810 | 10/1985 | Japan. |
| 61-207312 | 9/1986 | Japan. |
| 62-19511 | 1/1987 | Japan. |
| 64-22810 | 1/1989 | Japan. |
| 2-62810 | 3/1990 | Japan. |
| 3-63211 | 3/1991 | Japan. |
| 861463 | 2/1961 | United Kingdom. |

OTHER PUBLICATIONS

Y. Hosokawa et al., "Investigations on Pantothenic Acid and Its Related Compunds.XVIII.Chemical Studies.Synthesis of Pantothenyl Alcohol 4'-Phosphate", Chem. Pharm. Bull., vol. 17, No. 1, (1969), pp. 202–206.

V. Gilard et al., "Chemical and Biological Evaluation of Hydrolysis Products of Cyclophosphamide" J. Med. Chem., vol. 37, (1994), pp. 3986–3993.

Cherbuliez, et al. "Recherches sur la formation et la transformation des esters LXXI Sur la préparation des acides w–(phénylthiocarbamylamino)–alcoyl–phosphoriques et sur leur scission à divers pH" *Helvetica Chimica Acta* 49:2608–2614 (1966).

*Primary Examiner*—Michael G. Ambrose
*Attorney, Agent, or Firm*—Foley & Lardner

[57] ABSTRACT

Disclosed herein is a method for preparing 3-aminopropane phosphoric acid represented by the formula (I), comprising the steps of (a) reacting 3-amino-1-propanoi with phosphorus oxychloride at a low temperature, and (b) hydrolyzing the product of the step (a) in the presence of an acidic catalyst, and a cosmetic composition containing 3-aminopropanic phosphoric acid or its salts as an active ingredient.

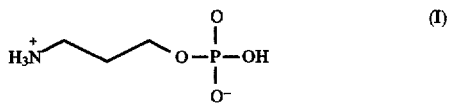

(I)

7 Claims, No Drawings

METHOD FOR PREPARING 3-AMINOPROPANE PHOSPHORIC ACID

BACKGROUND OF THE INVENTION

1. Field of the Invention

The present invention relates to a method for preparing 3-aminopropane phosphoric acid represented by the formula (I) and to cosmetic compositions containing it or its salts. More particularly, the present invention relates to a method for preparing 3-aminopropane phosphoric acid comprising steps of: (a) reacting 3-amino-1-propanol with phosphorus oxychloride at a low temperature, and (b) hydrolyzing the product of the step (a) in the presence of an acidic catalyst. The method provided by the present invention is simpler and more economic by virtue of the employment of two steps and of the employment inexpensive phosphorus oxychloride. Further, the present invention relates to cosmetic compositions containing 3-aminopropane phosphoric acid or its salts as an active ingredient. The compositions provided by the present invention can increase moisture retention ability, recuperation ability against the metamorphosis and firmness, of the skin, and thereby can defer skin aging effectively.

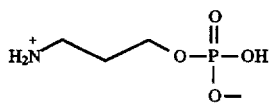

The function of the cosmetics is to keep skin or hair clear, beautiful and healthy. Particularly, there are many studies as to the cosmetics that can prevent skin wrinkling by activating the skin cells. As a result, many materials have been reported and used as a cosmetic ingredient. For example, there are vitamins such as retinol and ascorbic acid, extracts containing proteins, and flavonoids from various plants or animals, amino acid, epidermal growth factor, or α-hydroxy acid such as citric acid. However, it was well known that most of them are unstable in a cosmetic composition and irritative to the skin.

Under this circumstance, many studies have been conducted to provide a new material at itself is stable sufficient to be easily applied to the cosmetics and can promote cell-growth and synthesis of the epidermal collagen. For example, γ-aminobutyric acid (GABA: $H_2NCH_2CH_2CH_2COOH$) has been reported and used as a cosmetically active material. GABA is a taurine-like compound having a similar structure to that of taurine ($H_2NCH_2CH_2SO_3$)(MARTINDAL, The Extra Pharmacopeia. 29th, The Pharmaceutical Press) which has been known as a medical agent for diseases related with blood circulations of heart. It has been reported that GABA can suppress the skin wrinkle and has the skin whitening activity in JP-3-63211A, JP-2-62810A, JP-1-22810A, JP-62-19511A, JP-62-207312A, JP-60-199810A, JP-62-7162A and JP-58-26726A. But, GABA has a drawback that it can not provide satisfactory skin-aging suppressing action when it is formulated into cosmetic products.

Therefore, the present inventors have conducted extensive studies in order to provide cosmetics which can prevent the skin wrinkling and suppress the skin aging effectively. They have studied for an active material which does not cause skin irritation and is stable to be easily formulated into the cosmetic products, as well as can promote cell-growth and synthesis of the epidermal collagen. As a result, they found that the above objective can be accomplished by 3-aminepropane phosphoric acid(3-APPA; $H_2NCH_2CH_2CH_2OPO_3H$) having a structure that carboxyl group (—COOH) of γ-amminobutyric acid is substituted with phosphoric acid group (—$OPO_3H$) which is similar is sulfonic acid group (—$OSO_2H$) of taurine and has better skin-affinity than sulfonic acid group, and by cosmetic products containing it as an active ingredient.

Meanwhile, the conventional method for preparing 3-aminopropane phosphoric acid comprised steps of(a) reacting 3-amino-1-propanol with polyphosphoric acid at 150°~250° C. under reduced pressure for 30-40 hours, (b) reacting the product of the step (a) with calcium hydroxide ($Ca(OH)_2$) or barium hydroxide ($Ba(OH)_2$), and (c) neutralizing the salt obtained in the step (b) with sulfuric acid. But, in this method, since the reaction should be carried out at a high temperature (150°~250° C.) for a long period of time(30-40 hours), an energy consumption is high and the yield is low, and further it needs a complex purification step for removing calcium or barium salts produced during the removal of excessive phosphoric by-products.

In other method, 3-aminopropane phosphoric acid is produced by reacting 3-formamidopropanol with cyanoethyl phosphoric acid in the presence of dicyclohexylcarbodiimide; DCC); neutralizing the product with barium hydroxide and hydrolyzing with sodium hydroxide to produce barium salt, converting it to formamidopropyl phosphoric acid with cation exchange resin (amberlite IR 120($H^+$)), and hydrolyzing it with hydrochloric acid. This method is described in Chem. Pharm. Bull., 1969, 17(1), 202–206.

Further, as can be seen from the reaction scheme (I) of the conventional method, 3-aminopropane phosphoric acid is produced by reacting 3-aminopropanol with dichlorophosphoric acid phenyl ester at room temperature, purifying the product by passing it through a silica gel column to obtain a compound of formula (III), hydrolyzing this compound with hydrochloric acid, and reacting the product with platinous oxide and hydrogen. This method is described in J. Med. Chem., 1994, 37, 3986–3993.

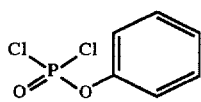

(II)

1. 3-Aminopropanol
2. Triethylamine

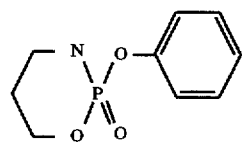

(III)

$H_2O, HCl$

-continued

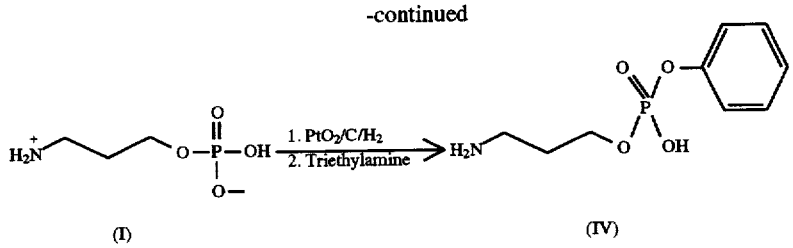

However, these methods give a low yield of 38% or less and comprise complex steps. Specially, the method described in J. Med. Chem. is not economic due to the expensive platinous oxide. Besides, in this method, dephenylesteration in the presence of hydrogen and platinous oxide needs a special apparatus. Therefore, this method is not suitable for industrial scale In a short word, the conventional methods are uneconomical and unsuitable for industrial applications due to a high cost of agents including catalysts and complex purification steps.

Under this circumstance, the present inventors have conducted extensive studies to provide a new method for preparing 3-aminopropane phosphoric acid which does not employ expensive agents, and of which process is simple and yield is high. As a result, this objective can be accomplished by using phosphorus oxychloride which can be purchased at a low cost.

SUMMARY OF THE INVENTION

Thus, an object of the invention is to provide a method for preparing 3-aminopropane phosphoric acid represented by formula (I):

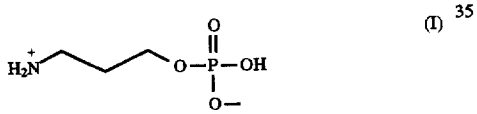

Further, other object of the invention is to provide cosmetic compositions containing 3-aminopropane phosphoric acid obtained by this method or its salts as an active ingredient, which can prevent skin wrinkling and defer skin aging effectively.

These objects can be accomplished by reacting 3-amino-1-propanol with phosphorus oxychloride in an organic solvent, and more particularly, the method according to the present invention is characterized in that it comprises steps of (a) reacting 3-amino-1-propanol with phosphorus oxychloride in an equivalent ratio of 1:1~1.3 in an organic solvent, at a temperature of 0°~5° C. for about 1 hour; (b) hydrolyzing the product of the step (a) in the presence of an acidic catalyst; and (c) recrystallizing the product of the step (b) with an alcohol.

Further, the cosmetic compositions according to the present invention is characterized in that they contain 3-aminopropane phosphoric acid obtained by the method or its salts in an amount of 0.001~20% by weight, based on a total weight of the compositions.

DETAILED DESCRIPTION OF THE INVENTION

The method according to the present invention comprises steps of:

(a) reacting 3-amine-1-propanol with phosphorus oxychloride in an equivalent ratio of 1:1~1.3 in an organic solvent, at a temperature of 0°~5° C. for about 1 hour;

(b) filtering the mixture of the step (a), concentrating the filtrate under reduced pressure and hydrolyzing the concentrate in the presence of an acidic catalyst; and (c) recrystallizing the product of the step (b) with an alcohol.

The method may be represented by the following reaction Scheme (II):

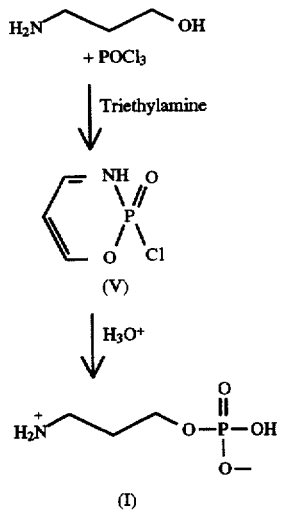

In detail, as shown in the above reaction scheme (II), 3-amino-1-propanol is reacted with phosphorus oxychloride in an organic solvent, at a temperature of 0°~5° C. for about 1 hour, to produce a cyclic phosphoramidyl chloride represented by formula (V). Then, the resulting reaction mixture is filtered and concentrated under reduced pressure. To the concentrate, water and an acidic catalyst are added, and the resulting mixture is heated to a temperature of 70°~90° C. and refluxed for 1~3 hours, preferably for 2 hours, and then cooled to a room temperature. The mixture is neutralized with a base, for example triethylamine. Finally, 3-aminopropane phosphoric acid is crystallized with an alcohol.

It is preferable that the reaction between 3-amino-1-propanol and phosphorus oxychloride is carried out in an equivalent ratio of 1:1~1.3. In case of the ratio is lower than 1:1, the objective product can not be obtained. While, in case of the ratio is higher than 1:1.3, excessive by-products as well as the objective product are obtained.

In this method, in the step (a), an intermediate 1:1 complex of 3-amino-1-propanol and phosphorus oxychloride is produced 95% or more, and a 2:1 complex by-product of 3-amino-1-propanol and phosphorus oxychloride is produced 1~2% or less. However, the by-product may be removed by chromatography or crystallization with an alcohol. Specially, two of three chlorine atoms of phosphorus oxychloride are replaced by functional hydroxyl and amino groups of 3-amino-1-propanol, and cyclized to a phosphoramidyl chloride. And, the third chlorine atom is inactivated at a low temperature of 5° C. or less and is not replaced. The reason is that the chlorine atom of the phosphoramidyl chloride is stable in an inert anhydrous solvent and not replaced easily by 3-amino-1-propanol. Therefore, the method can prevent the production of the 2:1 by-product of 3-amino-1-propanol and phosphorus oxychloride, by reacting 3-amino-1-propanol with phosphorus oxychloride in an equivalent ratio of 1:1~1.3, at a temperature of 0°~5° C. for about 1 hours. Especially, in the present invention, since the third chlorine atom of phosphorus oxychloride, is not required to be protected by, for example ester groups or amide groups, the process can be carried out in a simple and easy way.

The organic solvent employed in the method may include, but not limited thereto, dichloromethane, tetrahydrofuran, ethyl acetate, acetonitrile, ethyl ether and other inert solvents. It is preferable that the reaction should be carried out under an anhydrous condition, for example in an inert gas such as nitrogen or argon gas, in order to increase the yield.

Further, it is preferable that the reaction should be carried out at a temperature of 0°~5° C. In case of the temperature is higher than 5° C., two equivalents or more of 3-amino-1-propanol are substituted to phosphorus oxychloride, resulting in an increase of the amount of by-products. While, in case of the temperature is lower than 0° C., the solubility of reactant may be decreased and the reaction may proceed slowly and with difficulty. In this case, the amount of unreacted starting materials increased, resulting in a decrease of the yield.

The acidic catalyst employed in the present invention may include, but not limited thereto, hydrochloric acid, sulfuric acid and acetic acid. This acidic catalyst may be used in an mount of 5.0~10.0% by mole, preferably 5.0~7.0% by mole, based on the amount of the phosphoramidyl chloride represented by the formula (V). In case of 5% or less, total yield is decreased, while in case of 10% or more, the product may be colorated.

In this method, after adding water and an acidic catalyst, the resulting reaction mixture is heated to a reflux at a temperature of 70°~90° C. for the purpose of selective phosphorylation of alcohol group by hydrolyzing the bond between phosphorus and amine group. This is based on the general feature that the bond between phosphorus and amine group is weaker than that between phosphorus and alcohol group.

An alcohol employed in the present invention may include, but not limited thereto, methanol, ethanol and isopropanol. In the method, the use of an alcohol as a solvent for recrystallization is based on the fact that triethylammonium chloride produced by neutralization of triethylamine is soluble in an alcohol, but the product, 3-aminopropane phosphoric acid is insoluble and crystallized.

The method of preparation of 3-aminopropane phosphoric acid according to the present invention is simple and economic, because it employs two-step process and inexpensive phosphorus oxychloride, thereby it can be applied to an industrial scale.

Further, the present invention can provide cosmetic compositions containing 3-aminopropane phosphoric acid produced by the above-described method as an active ingredient, which can increase moisture retention ability, recuperation ability against the metamorphosis and firmness, of the skin, thereby deferring a skin aging effectively. The compositions contain 3-aminopropane phosphoric acid or its salts in an amount of 0.001~20% by weight, preferably 0.1~5% by weight.

3-Aminopropane phosphoric acid provided by the above-described method has a good solubility in water, so that it can be employed in any type cosmetic compositions as far as they contain some water. Further, it may be preferably employed in the form of salts obtained by neutralization, because the acid itself has a low pH. They may be exemplified by salts by alkaline metal such as sodium and potassium; salts by alkaline earth metal such as calcium and magnesium; salts by basic amino acids such as lysine, arginine and histidine; salts by ammonia or amides such as triethanol amine; salts by cationic polymers such as polyquaternium-4, -6, -7, -10, -11 and -16; and salts by cationic surfactants such as lauryldimethylbenzyl ammonium chloride and stearyldimethylbenzyl ammonium chloride.

PREFERRED EMBODIMENT OF THE INVENTION

The present invention will be described in more detail by way of the following examples. However, these examples are provided for only illustration purpose and should not be construed as limiting the scope of the invention, which is properly delineated in the accompanying claims.

(Preparation)

In a 2 l flask equipped with a stirrer and nitrogen gas injector, were introduced 112 g of phosphorus oxychloride and 650 ml of dichloromethane. Then, nitrogen gas was injected into the flask and the mixture was cooled to 0°~5° C. in an ice bath. In another reactor, 50 g of 3-amino-1-propanol and 186 ml of triethylamine were diluted with 180 ml of dichloromethane and added to the mixture for 30 min. After the addition, the mixture was stirred for other 30 min, and then filtered to remove triethylammonium chloride. The filtrate was concentrated under reduced pressure, and then transferred to a 1 l flask equipped with a reflux apparatus. 300 ml of water and 3 ml of c-HCl were added thereto and then the mixture was refluxed and heated for 2 hours. The mixture was cooled to a room temperature, and 90 ml of triethylamine was added thereto. Afar, the mixture was stirred at room temperature and 800 ml of ethanol was added thereto, and then filtered to recover crystals. Then, the crystals were recrystallized with a mixture of water and ethanol. The product was dried at 50° C. and under reduced pressure to a moisture content of 5% or less to recover 93 g of 3-aminopropane phosphoric acid (Yield: 90%).

Melting Point: 203°~206° C. (dec.) $^1$H-NMR(D$_2$O): δ(ppm)=1.9(m, 2H), 3.1(t, 2H), 3.9(q, 2H) $^{13}$C-NMR(D$_2$O): 67(ppm)=40.5(s), 30.6(d, 6.6), 65.8(d, 5.3)

(EXPERIMENTAL EXAMPLE 1)

The Activity of 3-amminopropane Phosphoric Acid

In order to evaluate the activity of 3-aminopropane phosphoric acid (3-APPA) on the skin, it is tested in vitro for effect on file proliferation of fibroblast and biosynthesis of collagen, and compared with those of ascorbic acid. And, in order to examine the effect thereof when applied onto the skin, a morphologic observation was carried out by using hairless mice.

(1-1) Proliferation of Fibroblast

The skin obtained from new epidermal tissue was treated with Type 1 collagenase to remove epidermis. The obtained fibroblast was cultured on Dulbecco's modified Eagle's media (DMEM).

The measurement of the mount of fibroblast was carried out by way of MTT method. The results are shown in Table 1. The score is calculated by considering the mount of fibroblast cultured on the medium without my additive as "100".

TABLE 1

| Concentration (%) | 0.00001 | 0.000001 | 0.0000001 |
|---|---|---|---|
| 3-APPA | 180 | 202 | 133 |
| Ascorbic acid | 128 | 149 | 138 |

As shown in the above Table 1, 3-aminopropane phosphoric acid is effective in proliferating fibroblast.

(1-2 Biosynthesis of Collagen $^3$H-Proline was added into a culture medium and cultured, and then the collagen was isolated from the medium using Type 1 collagenanse.

The promoting effect for synthesis of collagen was examined by comparing amounts of isotope. The results are shown in Table 2. The score is calculated by considering the amount of isotope cultured on the medium without any additive as "100".

TABLE 2

| Concentration (%) | 0.00001 | 0.000001 | 0.0000001 |
|---|---|---|---|
| 3-APPA | 111 | 146 | 124 |
| Ascorbic acid | 103 | 103 | 120 |

As shown in the above table 2, 3-aminopropane phosphoric acid is effective in promoting biosynthesis of collagen.

(1-3) Biosynthesis of Collagen When Applied Onto the Skin

Onto the back of hairless mice aging 8 weeks, cosmetic facial cream bases without and with 1% of 3-APPA were applied in the morning and night for 3 weeks, and then epidermal tissues were isolated. The tissues colored by an immunohistologic a coloring method with coloring kit of type 1 pN collagen antibody and ABC (Avidin-biotin peroxiclase complex). The results showed that biosynthesis of collagen is more active in case of the facial cream base added with 3-APPA than case of the facial cream without any additives.

(EXPERIMENTAL EXAMPLE 2)

Safety of 3-aminopropane Phosphoric Acid in the Living Body

Because cosmetic materials are applied onto the skin, their safety in the living body is important. In the present invention, toxicity and irritation of 3-APPA to the body were examined through the following experiments. The result proved that 3-APPA was safe to the living body.

All the rests were carried out using a mixture containing 3-APPA, glycerylpolymetacrylate, glycerine and water (1:1.5:1:6.5 by weight).

(2-1) Acute Oral Toxicity Test in Mice 1 ml/kg of 3-APPA mixture was administrated into the ten (10) of mice (five males and five females). There were no dead mice and no difference in the change of weights before or after administration.

(2-2) Acute Dermal Toxicity Test in Mice and Rabbits 1 ml/kg of 3-APPA mixture was dermal administrated into the ten (10) of mice (five males and five females) and observed for 2 weeks. There were no abnormal symptoms and no difference in the change of weights before or after admninistration. The same experiment was carried out using rabbits and the same results were obtained.

(2-3) Primary Skin Irritation Test

Twelve (12) of rabbits were treated by removing hairs of the back before 24 hours before the application of the test sample onto the skin. 0.1 ml of 3-APPA mixture was applied onto the back of each rabbit in 2.5 cm×2.5 cm and observed for 24 hours. No irritation was observed.

(2-4) Eye Irritation Test

3-APPA mixture was diluted with saline to give 2% test sample. Then, 0.1 ml of test sample was dropped onto one eye of each rabbit. As a result, no eye irritation on cornea, iris and conjunctiva was observed.

(2-5) Skin Sensitization Test

Test was earned out using six (6) of Guinea pigs (male 3 and female 3) according to Magnusson and Kligman's procedure. As a result, no skin abnormality such as erythema and edema was observed. And, according to the Kligman's criterion, grade one was given to 3-APPA, indicating that 3-APPA is very safe to the skin.

(2-6) Human Patch Test

Test was carried out for thirty (30) of healthy females aging 20~28 years according to CTFA Guideline (The cosmetic toiletry and Fragrance Association, Inc., Washington, D.C., 20036, 1991). As a result, no skin primary irritation was observed. Erythema irritation was observed for four among thirty females, just after the application, at a ratio of 4/30, but after 48 hours, all the irritation fade away.

(2-7) Repeat Insult Human Patch Test

Test was carried out according to CTFA Guideline. As a result, no repeat irritation or no sensitive irritation was observed.

Through the above experiments, it is estimated that 3-aminopropane phosphoric acid is a safe material for topical applications on the skin.

(Examples 1-2 and Comparative Examples 1-3) Moisture Cream

| Material | Ex. 1 | Ex. 2 | C. Ex. 1 | C. Ex. 2 | C. Ex. 3 |
|---|---|---|---|---|---|
| Stearic acid | 2.0 | 2.0 | 2.0 | 2.0 | 2.0 |
| Glyceryl monostearate | 3.0 | 3.0 | 3.0 | 3.0 | 3.0 |
| Cetostearyl alcohol | 3.0 | 3.0 | 3.0 | 3.0 | 3.0 |
| Squalane | 20.0 | 20.0 | 20.0 | 20.0 | 20.0 |
| Macademia nut oil | 10.0 | 10.0 | 10.0 | 10.0 | 10.0 |
| Silicone oil | 3.0 | 3.0 | 3.0 | 3.0 | 3.0 |
| Polysorbate-60 | 2.5 | 2.5 | 2.5 | 2.5 | 2.5 |
| Grycerin | 10.0 | 10.0 | 10.0 | 10.0 | 10.0 |
| Preservative | q.s. | q.s. | q.s. | q.s. | q.s. |

-continued (Examples 1~2 and Comparative Examples 1~3) Moisture Cream

| Material | Ex. 1 | Ex. 2 | C. Ex. 1 | C. Ex. 2 | C. Ex. 3 |
|---|---|---|---|---|---|
| Perfume | q.s. | q.s. | q.s. | q.s. | q.s. |
| Antioxidant | q.s. | q.s. | q.s. | q.s. | q.s. |
| 3-APPA* | 5.0 | — | — | — | — |
| Ammonium 3-APPA | — | 5.0 | — | — | — |
| 3-APS* | — | — | 5.0 | — | — |
| Taurine | — | — | — | 5.0 | — |
| GABA* | — | — | — | — | 5.0 |
| Distilled Water | to 100 | to 100 | to 100 | to 100 | to 100 |

(Note)
3-APPA: 3-Aminopropane phosphoric acid
3-APS: 3-Aminopropane sulfonic acid
GABA: γ-Aminobutyric acid (Examples 3~4 and Comparative Examples 4~6) Emollient Lotion

| Material | Ex. 3 | Ex. 4 | C. Ex. 4 | C. Ex. 5 | C. Ex. 6 |
|---|---|---|---|---|---|
| Stearyl alcohol | 0.5 | 0.5 | 0.5 | 0.5 | 0.5 |
| Monostearic grycerin | 2.0 | 2.0 | 2.0 | 2.0 | 2.0 |
| Squalane | 20.0 | 20.0 | 20.0 | 20.0 | 20.0 |
| Polysorbate-60 | 2.0 | 2.0 | 2.0 | 2.0 | 2.0 |
| Sorbitan stearate | 0.5 | 0.5 | 0.5 | 0.5 | 0.5 |
| Grycerin | 5.0 | 5.0 | 5.0 | 5.0 | 5.0 |
| Preservative | q.s. | q.s. | q.s. | q.s. | q.s. |
| Perfume | q.s. | q.s. | q.s. | q.s. | q.s. |
| Antioxidant | q.s. | q.s. | q.s. | q.s | q.s. |
| Lysine 3-APPA | 1.0 | — | — | — | — |
| Calcium 3-APPA | — | 1.0 | — | — | — |
| 3-APS | — | — | 1.0 | — | — |
| Taurine | — | — | — | 1.0 | — |
| GABA | — | — | — | — | 1.0 |
| Distilled Water | to 100 | to 100 | to 100 | to 100 | to 100 |

(EXPERIMENTAL EXAMPLE 3)

Safety to the Skin

In order to evaluate safety of cosmetic composition containing 3-aminepropane phosphoric acid or its salts onto the skin, the conventional patch test was carried out for compositions of Examples and Comparative Examples, and the level of skin irritation was estimated according to the following scoring system:

| | |
|---|---|
| +++ | Extremely severe irritation, estimated to be inadequate as a cosmetic |
| ++ | Severe irritation, estimated to be better not to use as a cosmetic |
| + | A little irritation, estimated to be carefully used as a cosmetic |
| ± | Little irritation |
| − | No irritation, estimated to be adequate for the sensitive skin |
| = | No irritation in repeat application |

TABLE 3

| Material | Ex. 1 | Ex. 2 | C. Ex. 1 | C. Ex. 2 | C. Ex. 3 |
|---|---|---|---|---|---|
| Evaluation | = | = | + | + | + |
| Material | Ex. 3 | Ex. 4 | C. Ex. 4 | C. Ex. 5 | C. Ex. 6 |
| Evaluation | = | = | + | + | + |

(EXPERIMENTAL EXAMPLE 4)

Moisture Retention Ability

Test was carried out by measuring skin hydration with Comeometer before application and after 1 hour application. The result was shown as percentage.

TABLE 4

| Material | Ex. 1 | Ex. 2 | C. Ex. 1 | C. Ex. 2 | C. Ex. 3 |
|---|---|---|---|---|---|
| Hydration | 93% | 90% | 85% | 64% | 74% |
| Material | Ex. 3 | Ex. 4 | C. Ex. 4 | C. Ex. 5 | C. Ex. 6 |
| Hydration | 96% | 94% | 89% | 77% | 79% |

(EXPERIMENTAL EXAMPLE 5)

Skin Extensibility

Evaluation for skin extensibility in this experiment and evaluations for skin tonicity and skin firmness in the following experiments were carried out by checking the state of the skin with Fermometer.

Ten (10) groups were composed of four (4) of females aging 21~36 years. Each group used one test composition for 4 weeks. The skin state was checked before, after 2 weeks and after 4 weeks. The result was shown as percentage.

TABLE 5

| Material | Ex. 1 | Ex. 2 | C. Ex. 1 | C. Ex. 2 | C. Ex. 3 (%) |
|---|---|---|---|---|---|
| after 2 weeks | +8 | +8 | +7 | +5 | +8 |
| after 4 weeks | +15 | +17 | +12 | +9 | +10 |
| Material | Ex. 3 | Ex. 4 | C. Ex. 4 | C. Ex. 5 | C. Ex. 6 |
| after 2 weeks | +10 | +11 | +9 | +6 | +7 |
| after 4 weeks | +17 | +17 | +14 | +8 | +11 |

(EXPERIMENTAL EXAMPLE 6)

Tonicity

TABLE 6

| Material | Ex. 1 | Ex. 2 | C. Ex. 1 | C. Ex. 2 | C. Ex. 3 (%) |
|---|---|---|---|---|---|
| after 2 weeks | +18 | +19 | +15 | +9 | +14 |
| after 4 weeks | +32 | +33 | +25 | +19 | +21 |
| Material | Ex. 3 | Ex. 4 | C. Ex. 4 | C. Ex. 5 | C. Ex. 6 |
| after 2 weeks | +20 | +18 | +14 | +11 | +14 |
| after 4 weeks | +37 | +34 | −24 | +18 | +20 |

(EXPERIMENTAL EXAMPLE 7)

Skin Firmness

TABLE 7

| Material | Ex. 1 | Ex. 2 | C. Ex. 1 | C. Ex. 2 | C. Ex. 3 (%) |
|---|---|---|---|---|---|
| after 2 weeks | +9 | +8 | +6 | +6 | +6 |
| after 4 weeks | +14 | +15 | +9 | −8 | +9 |

TABLE 7-continued

| Material | Ex. 3 | Ex. 4 | C. Ex. 4 | C. Ex. 5 | C. Ex. 6 (%) |
|---|---|---|---|---|---|
| after 2 weeks | +10 | +12 | +9 | +6 | +8 |
| after 4 weeks | +18 | +19 | +14 | +8 | +10 |

From the results of tables 3~7, although the experimental error and the personal error was admitted, the compositions containing 3-aminopropane phosphoric acid or its salts are less irritant and more excellent in skin hydration, skin extensibility, skin tonicity and skin firmness than the compositions containing 3-aminopropane sulfonic acid, taurine or γ-aminobutyric acid.

(Example 5) Colorless Toilet Water

| Material | % by weight |
|---|---|
| Grycerin | 10 |
| Polysorbate-20 | 2 |
| Ethanol | 10 |
| Sodium 3-APPA | 2 |
| Perfume | q.s. |
| Preservative | q.s. |
| Antioxidant | q.s. |
| Emollient agent | q.s. |
| Distilled water | to 100 |

(Example 6) Cleansing Foam

| Material | % by weight |
|---|---|
| Stearic acid | 10 |
| Palmitic acid | 5 |
| Myristic acid | 15 |
| Lauric acid | 6 |
| KOH | 6 |
| Grycerin | 15 |
| Calcium 3-APPA | 0.5 |
| Perfume | q.s. |
| Preservative | q.s. |

-continued (Example 6) Cleansing Foam

| Material | % by weight |
|---|---|
| Nonionic surfactant | q.s. |
| Distilled water | to 100 |

What is claimed is:

1. A method for preparing 3-aminopropane phosphoric acid from 3-amino-1-propanol, which comprises the steps of:
   (a) reacting 3-amino-1-propanol with phosphorus oxychloride in an equivalent ratio of 1:1–1.3 in an organic solvent, at a temperature of 0°–5° C. for about 1 hour, to form a cyclic phosphoramidyl chloride intermediate;
   (b) hydrolyzing the intermediate of step (a) in the presence of an acidic catalyst;
   (c) recrystallizing the product of step (b) with an alcohol solvent; and
   (d) optionally forming a salt thereof.

2. The method as claimed in claim 1, wherein said organic solvent in said step (a) is selected from the group consisting of dichloromethane, tetrahydrofuran, ethyl acetate, acetonitrile and ethyl ether.

3. The method as claimed in claim 1, wherein in step (b), said acidic catalyst is hydrochloric acid, sulfuric acid or acetic acid.

4. The method as claimed in claim 3, wherein said acidic catalyst in step (b) is used in an amount of 5.0–10.0% by mole based on the amount of the intermediate produced in step (a).

5. The method as claimed in claim 1, wherein said alcohol in said step (c) is selected from the group consisting of methanol, ethanol and isopropanol.

6. The method as claimed in claim 1, wherein a salt is formed.

7. The method as claimed in claim 7, wherein said salt is an alkali metal salt, an alkaline earth metal salt, a salt of a basic amino acid, a salt of ammonia or an amine, a salt of a cationic polymer or a salt of a cationic surfactant.

* * * * *